US00RE46214E

(19) United States
(12) Reissued Patent
Qureshi et al.

(10) Patent Number: US RE46,214 E
(45) Date of Reissued Patent: Nov. 22, 2016

(54) METHOD AND SYSTEM FOR SAMPLE ALIQUOT STORAGE

(75) Inventors: Humayun Qureshi, Yorba Linda, CA (US); Bernhard Spless, Anaheim Hills, CA (US); Robert A. Weiss, Victoria, MN (US); Peter G. Werness, Carver, MN (US); Brian D. Wilson, Pleasant Hill, CA (US); Ronald C. Laska, Minnetonka, MN (US)

(73) Assignee: Beckman Coulter, Inc., Brea, CA (US)

(21) Appl. No.: 11/351,215

(22) Filed: Feb. 9, 2006

Related U.S. Patent Documents

Reissue of:
(64) Patent No.: 6,793,888
Issued: Sep. 21, 2004
Appl. No.: 09/908,169
Filed: Jul. 18, 2001

U.S. Applications:
(63) Continuation of application No. 09/815,088, filed on Mar. 16, 2001, now Pat. No. 6,825,041.

(51) Int. Cl.
*G01N 35/10* (2006.01)
*G01N 35/00* (2006.01)

(52) U.S. Cl.
CPC ..... *G01N 35/0092* (2013.01); *G01N 35/1002* (2013.01); *Y10T 436/11* (2015.01); *Y10T 436/113332* (2015.01); *Y10T 436/115831* (2015.01)

(58) Field of Classification Search
CPC ..... G01N 2001/002; G01N 2035/00178; G01N 2035/00316; G01N 2035/0446; G01N 35/0092; G01N 35/1002; Y10T 436/115831; Y10T 436/113332; Y10T 436/11
USPC ..... 422/63–67, 100, 501, 509, 510; 436/43, 436/47, 50, 180
See application file for complete search history.

(56) References Cited

U.S. PATENT DOCUMENTS 3,607,099 A 9/1971 Scordato et al.
4,091,323 A * 5/1978 Landis ..... 324/318

(Continued)

FOREIGN PATENT DOCUMENTS

JP 02025755 1/1990
JP 04-279862 10/1992

(Continued)

*Primary Examiner* — Elizabeth McKane
(74) *Attorney, Agent, or Firm* — Kilpatrick Townsend & Stockton LLP

(57) ABSTRACT

A method and system of sample aliquot storage for automated immunochemistry or chemistry instruments are provided. The method and system provide a sample aliquot storage unit having a sample storage wheel for storing sample vessels containing sample aliquots in a chilled enclosed environment, which are accessible by both a sample pipettor of a sample aliquoting station and a pick-and-place gripper. The pick-and-place gripper transports the sample vessels containing sample aliquots to multiple independent reagent pipetting stations respectively for sample aspiration of subsequent assay, and thereafter transports the sample vessels containing remaining sample aliquots back to the sample storage wheel to be stored in the chilled environment for reflex testing. When all the tests are completed, the pick-and-place gripper transports the sample vessels to a waste storage area.

37 Claims, 4 Drawing Sheets

(56) References Cited

U.S. PATENT DOCUMENTS 4,166,094 A 8/1979 Froehlich et al.
4,363,245 A 12/1982 Schmid
4,678,752 A 7/1987 Thorne et al.
4,834,944 A 5/1989 Wakatake
4,837,159 A 6/1989 Yamada
5,055,408 A 10/1991 Higo et al.
5,158,895 A 10/1992 Ashihara et al.
5,178,833 A 1/1993 Covain
5,182,083 A 1/1993 Barker et al.
5,204,269 A 4/1993 Barker et al.
5,215,714 A * 6/1993 Okada et al. ..... 422/64
5,229,074 A 7/1993 Heath et al.
5,236,666 A 8/1993 Hulette et al.
5,250,440 A 10/1993 Kelln et al.
5,305,650 A 4/1994 Koike et al.
5,350,564 A 9/1994 Mazza et al.
5,358,691 A 10/1994 Clark et al.
5,366,896 A 11/1994 Margrey et al.
5,380,487 A 1/1995 Choperena et al.
5,434,083 A 7/1995 Mitsumaki et al.
5,439,645 A * 8/1995 Saralegui et al. ..... 422/64
5,482,861 A 1/1996 Clark et al.
5,501,838 A 3/1996 Ootani et al.
5,575,976 A 11/1996 Choperena et al.
5,580,524 A 12/1996 Forrest et al.
5,587,129 A 12/1996 Kurosaki et al.
5,597,733 A 1/1997 Bell et al.
5,639,425 A * 6/1997 Komiyama et al. ..... 422/63
5,646,046 A 7/1997 Fischer et al.
5,658,799 A 8/1997 Choperena et al.
5,670,120 A 9/1997 Degenhardt et al.
5,693,292 A 12/1997 Choperena et al.
5,730,938 A 3/1998 Carbonari et al.
5,735,387 A * 4/1998 Polaniec ..... G01N 35/04 198/465.1
5,770,054 A 6/1998 Ardes
5,795,547 A * 8/1998 Moser et al. ..... 422/64
5,814,277 A 9/1998 Bell et al.
5,843,376 A * 12/1998 Ishihara et al. ..... 422/64
5,846,491 A 12/1998 Choperena et al.
5,856,193 A 1/1999 Fanning et al.
5,885,529 A 3/1999 Babson et al.
5,885,530 A 3/1999 Babson et al.
5,979,250 A 11/1999 Tanihata
5,989,499 A 11/1999 Catanzariti et al.
6,117,392 A * 9/2000 Hanawa ..... G01N 35/00603 422/65
6,117,683 A * 9/2000 Kodama et al. ..... 436/47
6,520,755 B1 2/2003 Kittock et al.
6,746,648 B1 6/2004 Mattila et al.
6,776,961 B2 * 8/2004 Lindsey et al. ..... 422/63
6,825,041 B2 11/2004 Qureshi et al.
6,843,481 B1 1/2005 Kittock et al.
2002/0102736 A1 8/2002 Kittock et al.
2002/0106305 A1 8/2002 Willenbring et al.
2002/0132356 A1 9/2002 Qureshi et al.
2002/0164269 A1 11/2002 Ngo et al.
2004/0175840 A1 9/2004 Devlin, Sr. et al.
2005/0013735 A1 1/2005 Gebrian et al.
2005/0013736 A1 1/2005 McKeever
2005/0013737 A1 1/2005 Chow et al.
2005/0013743 A1 1/2005 Farina et al.
2005/0013746 A1 1/2005 Lee et al.
2005/0013747 A1 1/2005 Huynh-Ba et al.
2005/0014272 A1 1/2005 Mizzer et al.
2005/0014274 A1 1/2005 Lee et al.
2005/0014285 A1 1/2005 Miller
2005/0071110 A1 3/2005 Davis
2005/0249634 A1 11/2005 Devlin, Sr.

FOREIGN PATENT DOCUMENTS

JP 04279862 10/1992
JP 08094629 4/1996
WO WO 93/12431 6/1993

* cited by examiner

METHOD AND SYSTEM FOR SAMPLE ALIQUOT STORAGE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED PATENT APPLICATION

This is a continuation of the U.S. patent application Ser. No. 09/815,088, entitled "Method and System For Automated Immunochemistry Analysis," filed on Mar. 16, 2001 *now U.S. Pat. No. 6,825,041,* the content of which is incorporated herein in its entirety.

BACKGROUND OF THE INVENTION

1. Area of the Art

The present invention relates generally to automated immunochemistry instruments and methodologies, and more particularly to methods and systems for sample aliquot storage used in connection with automated immunochemistry instruments.

2. Description of the Prior Art

Automated immunochemistry instruments are widely used in clinical chemistry sampling and analyzing applications for performing various assays. Such automated immunochemistry instruments often incorporate a sample aliquot unit for aliquoting samples to be analyzed. The following references are found to be pertinent to the field of the present invention:

U.S. Pat. No. 3,607,099 issued to Scordato et. al.;
U.S. Pat. No. 4,166,094 issued to Froehlich et al.;
U.S. Pat. No. 4,363,245 issued to Schmid;
U.S. Pat. No. 5,182,083 issued to Barker et al.;
U.S. Pat. No. 5,204,269 issued to Barker et al.;
U.S. Pat. No. 5,229,074 issued to Heath et al. ("Heath '074 patent");
U.S. Pat. No. 5,236,666 issued to Hullette et al.;
U.S. Pat. No. 5,350,564 issued to Mazza et al.;
U.S. Pat. No. 5,366,896 issued to Margrey et al.;
U.S. Pat. No. 5,580,524 issued to Forrest et al. ("Forrest '524 patent");
U.S. Pat. No. 5,587,129 issued to Kurosaki et al.;
U.S. Pat. No. 5,597,733 issued to Bell et al. ("Bell '733 patent");
U.S. Pat. No. 5,646,046 issued to Fischer et al.;
U.S. Pat. No. 5,670,120 issued to Degenhardt et al.;
U.S. Pat. No. 5,814,277 issued to Bell et al. ("Bell '277 patent"); and
U.S. Pat. No. 5,989,499 issued to Catanzariti et al.

The Forrest '524 patent disclosed an automated multi-test capability assay apparatus in modular form for the non-sequential processing of samples for the assay. The apparatus includes a device for ensuring solid phase suspension which includes a housing, a rotatable support having means for independently rotatably mounting a vessel around a circumference of the support, and a drive wheel for rotating the mounted vessel, where the housing includes a driving surface having longer circumferential dimensions than the drive wheel and surrounding the drive wheel and engageable therewith.

The Kurosaki '129 patent disclosed an apparatus for automatically analyzing a specimen. The apparatus includes a first dispensing means for dispensing the specimen in a sample vial into a stock vial, a second dispensing means for dispensing the specimen in the stock vial into an assay vial, and a third dispensing means for dispensing the reagent into the assay vial. A cooling device is provided below a stock vial turntable for cooling the specimens contained in the stock vials.

The Heath '074 patent, the Bell '733 patent, and the Bell '277 patent also disclosed various arrangements of using a turntable with a cooler for cooling the samples and reagent contained in the turntable.

While various sample aliquot units for automated immunochemistry instruments have been developed, as disclosed in the above references, there is still a need to create and develop a new sample aliquot and storage unit that can accommodate the following two new emerging trends that are evolving in the clinical laboratory. First, there is an increase in the use of automatic sample reflex testing. Second, the laboratory automation has increased the demands for the quick release of sample tubes. These two new trends require new sample aliquot units to be capable of storing the samples for reflex testing, while supporting the high throughput of the automated immunochemistry instruments.

SUMMARY OF THE INVENTION

The present invention is directed to a new method and system of sample aliquot storage for an automated immunochemistry instrument.

It is one of the primary objects of the present invention to provide a new method and system of sample aliquot storage for an automated immunochemistry instrument that is capable of performing automatic sample reflex testing.

It is also a primary object of the present invention to provide a new method and system of sample aliquot storage for an automated immunochemistry instrument that is capable of having a higher throughput.

It is another primary object of the present invention to provide a new method and system of sample aliquot storage for an automated immunochemistry instrument that is capable of working with multiple pipetting modules for running different samples simultaneously.

In addition, it is a primary object of the present invention to provide a new method and system of sample aliquot storage for an automated immunochemistry instrument that ensures sample integrity and low evaporation by incorporating an enclosed large capacity chilled sample storage area.

These and other objects and advantages may be achieved by a sample aliquot storage system of the present invention. In accordance with the embodiment of the present invention, a sample aliquot storage system of the present invention, which is used as part of an automated immunochemistry instrument, has a chilled storage for storing multiple sample vessels containing aliquoted samples that may be used for reflex testing. The sample vessels containing aliquoted samples can be moved to one of the multiple independent pipetting stations. Each of the multiple independent pipetting stations has a pipettor for aspirating a required amount of sample from the sample vessels and dispensing it into an reaction vessel. This allows the immunochemistry instruments to run different samples simultaneously (while their respective cycles may be offset in time).

Such an arrangement has been found to provide a number of advantages. As explained in greater detail below, the new method and system of sample aliquot storage of the present invention support automatic reflex testing of the samples as well as a high throughput of the automated immunochemistry instrument.

The new method and system of sample aliquot storage of the present invention also allow the immunochemistry instrument with multiple pipetting stations to run different samples simultaneously.

The system of the present invention may be used in connection with other chemical analyzers, such as, but not limited to, chemistry and hematology diagnostic instrumentation.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

The present invention is directed to a new method and system of sample aliquot storage for an automated immunochemistry instrument. The new system of the present invention includes a sample aliquot storage unit incorporated in the automated immunochemistry instrument, and the method of the present invention includes the procedures for storing and transporting sample vessels containing sample aliquots to be automatically reflex tested by the automated immunochemistry instrument.

Figure 1:
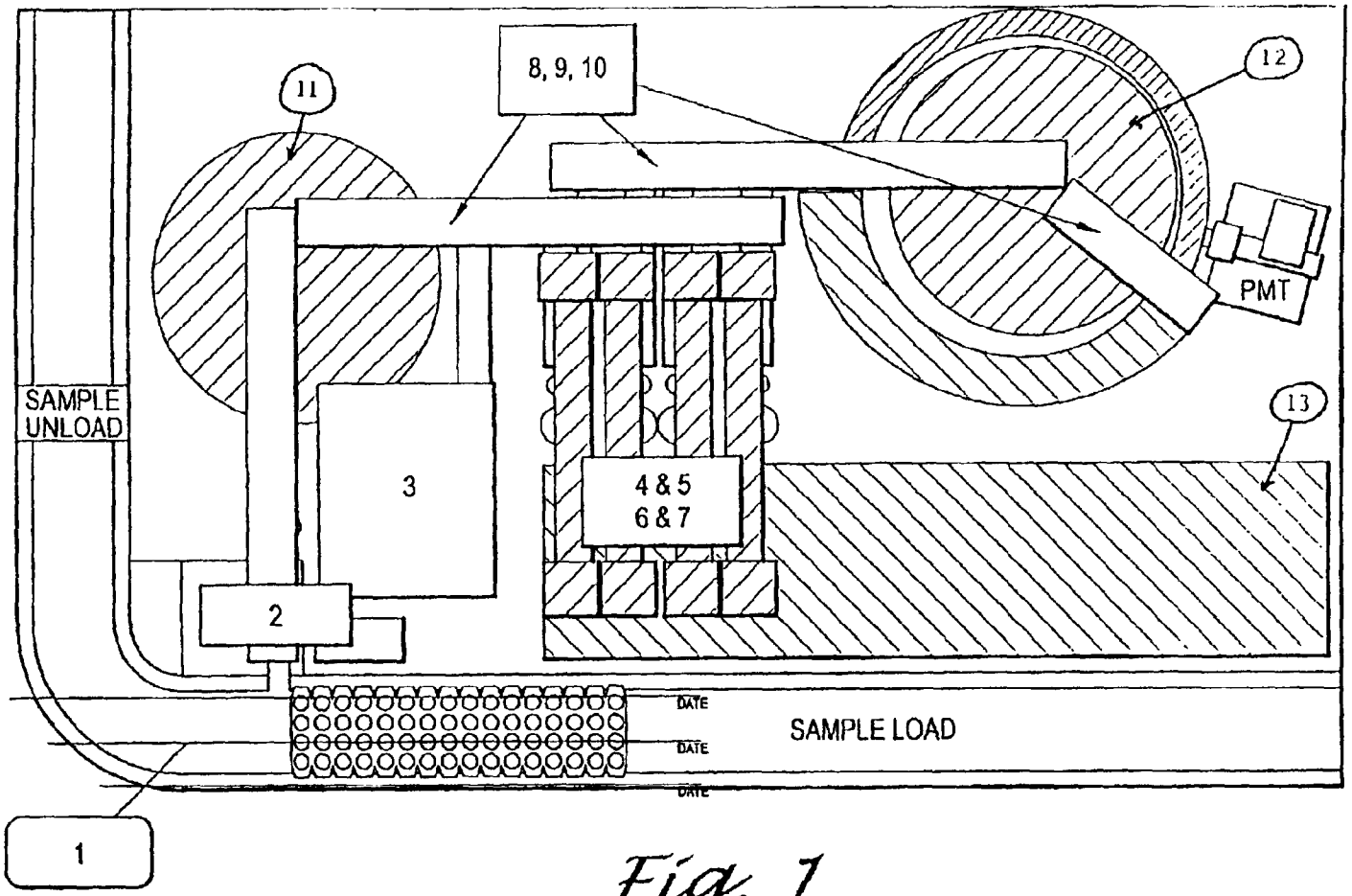
FIG. 1 is an illustrative block diagram showing the basic structural and functional modules of an automated immunochemistry instrument incorporating the sample aliquot storage system of the present invention.

Referring to FIG. 1, there is shown an illustrative block diagram demonstrating the basic structural and functional modules of the automated immunochemistry instrument, incorporating the sample aliquot storage of the present invention. A detailed description of the functions and operations of the automated immunochemistry instrument is provided in the Assignee's co-pending patent application for "Method and System For Automated Immunochemistry Analysis," Ser. No. 09/815,088, and the content of which is incorporated herein in its entirety by reference.

As shown in FIG. 1, the basic structural and functional modules of the automated immunochemistry instrument include a sample presentation unit 1, a main sample aliquoting station 2, a bulk vessel feeder 3, first dual reagent pipetting stations 4 and 5, second dual reagent pipetting stations 6 and 7, first pick-and-place gripper 8, a second pick-and-place gripper 9, a third pick-and-place gripper 10, a sample aliquot storage unit 11 of the present invention, an incubator/wash/read station 12, and a reagent storage 13.

The sample presentation unit 1 is used to transport the entire required test samples to and from the main sample aliquoting station 2. A detailed description of the configurations and functions of one embodiment of the sample presentation unit 1 is provided in the Assignee's co-pending patent application for "Sample Presentation Unit," Ser. No. 09/848,450, and is incorporated herein in its entirety by reference. However, it should be understood that other lab automation systems or automated track conveyance systems may also used as long as they are capable of transport the entire required test samples to and from the main sample aliquoting station 2.

The main sample aliquoting station 2 is used to aspirate sample aliquots out of the sample tubes and dispense them into sample vessels supplied by the bulk vessel feeder 3. A detailed description of the configurations and functions of one embodiment of the bulk vessel feeder 3 is provided in the Assignee's co-pending patent application for "Bulk Vessel Feeder," Ser. No. 09/777,750, and is incorporated herein by reference. However, it should be understood that other vessel supply mechanism that is capable of supplying sample vessels may also be used for the purpose of the present invention.

The four reagent pipetting stations 4, 5, 6, and 7 are used to mix sample aliquots with reagents for the subsequent assay. The four reagent pipetting stations 4, 5, 6, and 7 are arranged as two dual reagent pipetting stations and are independent to each other, each having its own fluid pumps and valves, wash towers, reaction vessel carriages, and pipettor. The individual structures and functions of each of these reagent pipetting stations 4, 5, 6, and 7 conform to existing arrangements used in the Access Instruments (Beckman Coulter, Inc., CA), which are known to those of ordinary skill in the art, and therefore will not be described in detail here.

The three vessel pick-and-place grippers 8, 9, and 10 are used to transport sample and reaction vessels among the various modules of the automated immunochemistry instrument. The first pick-and-place gripper 8 is used to transport sample vessels among the bulk vessel feeder 3, the sample aliquot storage unit 11, and the reagent pipetting stations 4, 5, 6, and 7. The second pick-and-place gripper 9 is used to transport reaction vessels between the reagent pipetting stations 4, 5, 6, and 7 and the incubator of the incubator/wash/read station 12. The third pick-and-place gripper 10 is used to transport reaction vessels between the incubator wheel and the wash wheel of the incubator/wash/read station 12. A detailed description of the configurations and functions of one embodiment of the vessel pick-and-place grippers 8, 9, and 10 is provided in the Assignee's co-pending patent application for "Method and System for Picking and Placing Vessels," Ser. No. 09/7771,471, and is incorporated herein in its entirety by reference. However, it should be understood that other pick-and-place mechanism that is capable of transporting sample and reaction vessels among the various modules of the automated immunochemistry instrument is also contemplated for the purpose of the present invention.

The sample aliquot storage unit 11 of the present invention is used for storing the sample aliquots contained in the sample vessels in a controlled environment enclosure at a low temperature for a certain period of time, e.g., up to three (3) hours, so that the samples may be used for reflex testing. When a test is requested on a patient sample, the test outcome may drive a request for additional testing. This automatic request for additional tests is reflex testing.

The time delay from the first aspiration to knowing if another test will be started can range to as long as 45 minutes or more. To hold a sample tube for such a period of time prevents the sample from being used in other places. If the tube is passed to other instruments, it may be difficult for a laboratory technician to find the tube and reload it on the instrument requesting the reflex test.

To allow a single quick sample draw on sample tubes that might require reflex testing, a single aspiration (aliquot) can be taken with sufficient test material for the possible reflex test(s). However, to insure that the test materials do not evaporate or deteriorate, the sample aliquots need to be enclosed and refrigerated on board the automated immunochemistry instrument.

Figure 2:
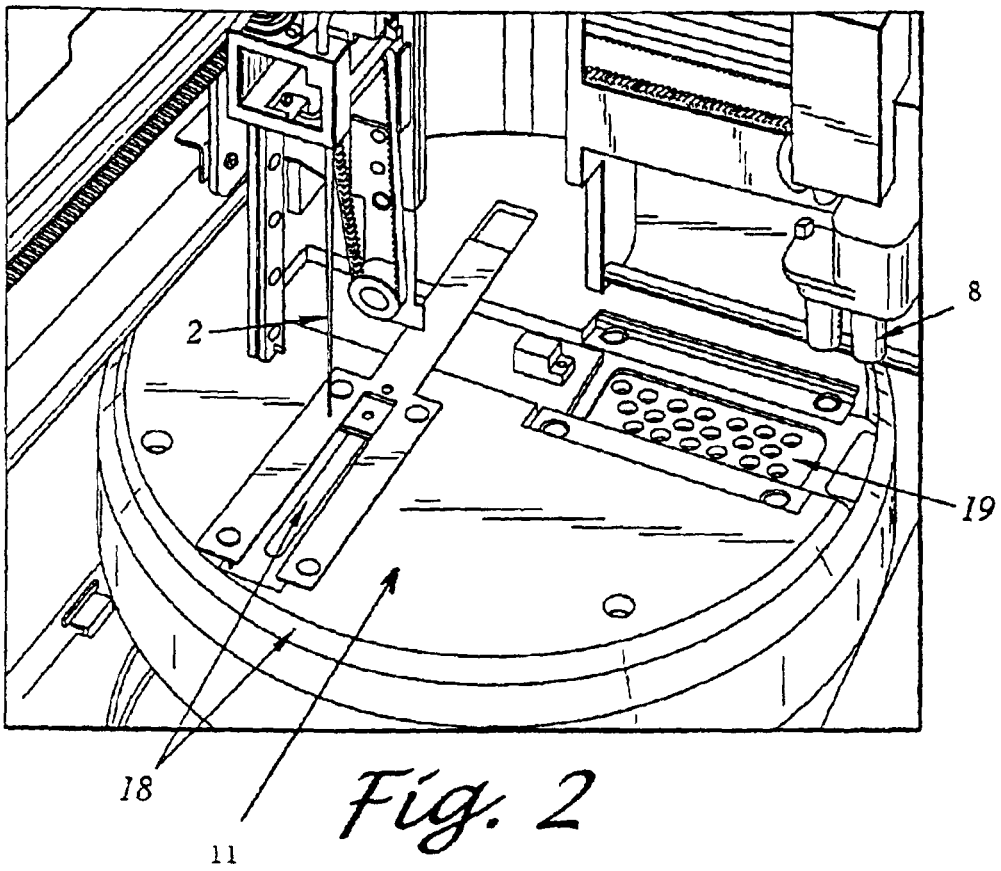
FIG. 2 is a perspective view showing the arrangement of the main sample pipetting station of the automated immunochemistry instrument and the sample aliquot storage system of the present invention incorporated in the automated immunochemistry instrument.

Referring to FIG. 2, there is shown the arrangement of the main sample aliquoting station 2 and the sample aliquot storage unit 11 of the present invention incorporated in the automated immunochemistry instrument. The pipettor of the main sample aliquoting station 2 first aspirates sample aliquots from the sample tubes presented by a sample presentation mechanism, such as the sample presentation unit or a lab automation conveyance system (not shown in FIG. 2), and then moves into a position above the sample aliquot storage unit 11. Meanwhile, the sample aliquot storage unit 11 receives an empty sample vessel from the bulk vessel feeder 3 by the pick-and-place gripper 8, and moves the empty sample vessel under the pipettor of the main sample aliquoting station 2. The aspirated sample aliquot is then dispensed into the empty sample vessel. Insulation and doors 18 are provided to control the environment in the chilled sample storage 11.

The sample aliquot storage unit 11 has a precision controlled and refrigerated (chilled) sample aliquot storage wheel 19 with multiple storage locations capable of receiving and transferring sample vessels for or filled with sample aliquots.

Figure 3:
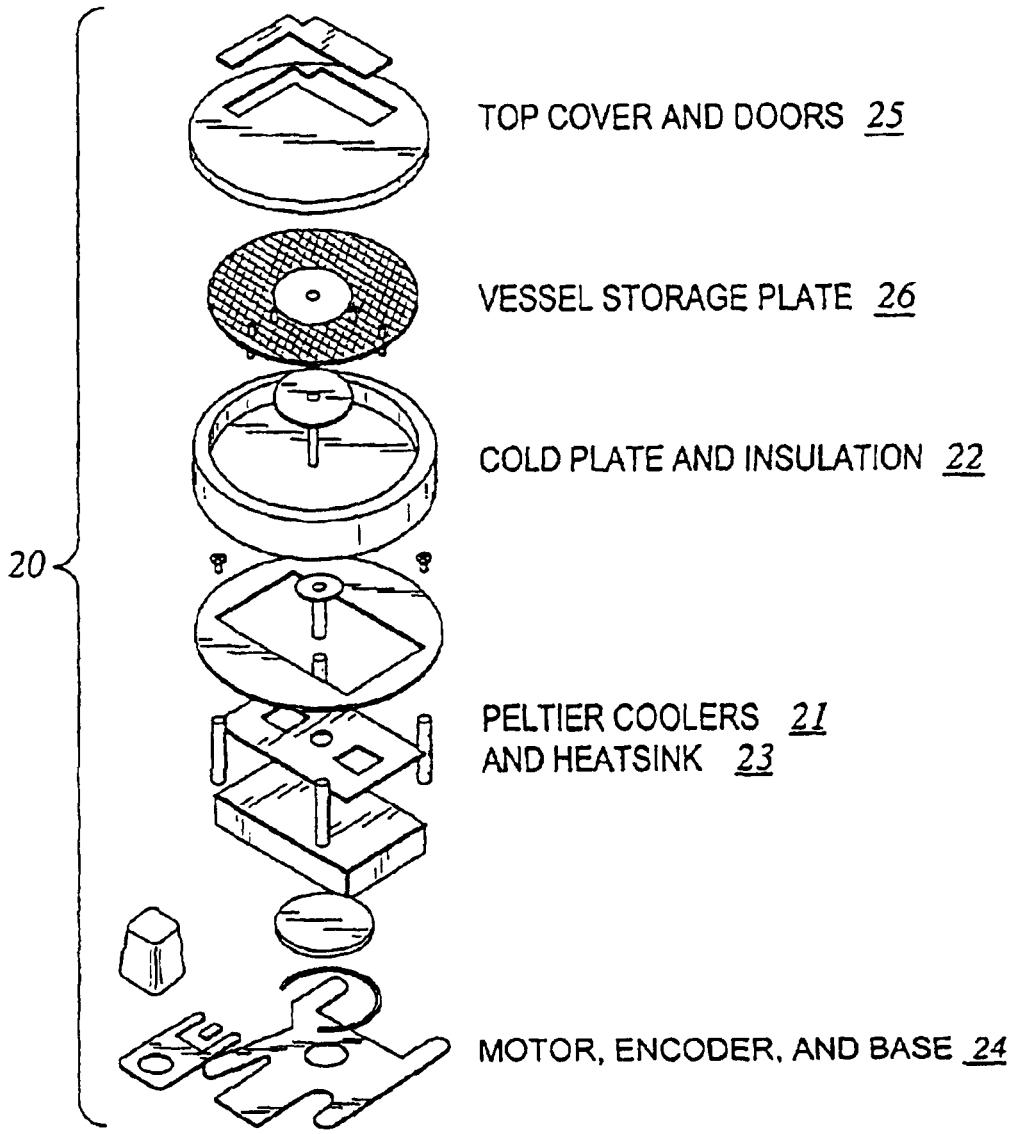
FIG. 3 is an exploded perspective view showing the arrangement of the sample aliquot chiller assembly of the sample aliquot storage system of the present invention.

Referring to FIG. 3, there is shown an arrangement of the sample aliquot chiller assembly 20 of the sample aliquot storage unit 11 of the present invention incorporated into the automated immunochemistry instrument. The construction of the sample aliquot chiller assembly 20 utilizes Peltier coolers 21 connected to a cold plate 22 and a heatsink 23. Heat is removed by blowing air over the heatsink 23. These components are mounted on a base 24 and insulated with covers and doors 25. Sample vessels containing sample aliquots are stored within the cooled area on a closed spaced storage plate 26 and kept in the cool environment until needed for testing or reflex testing.

Figure 4:
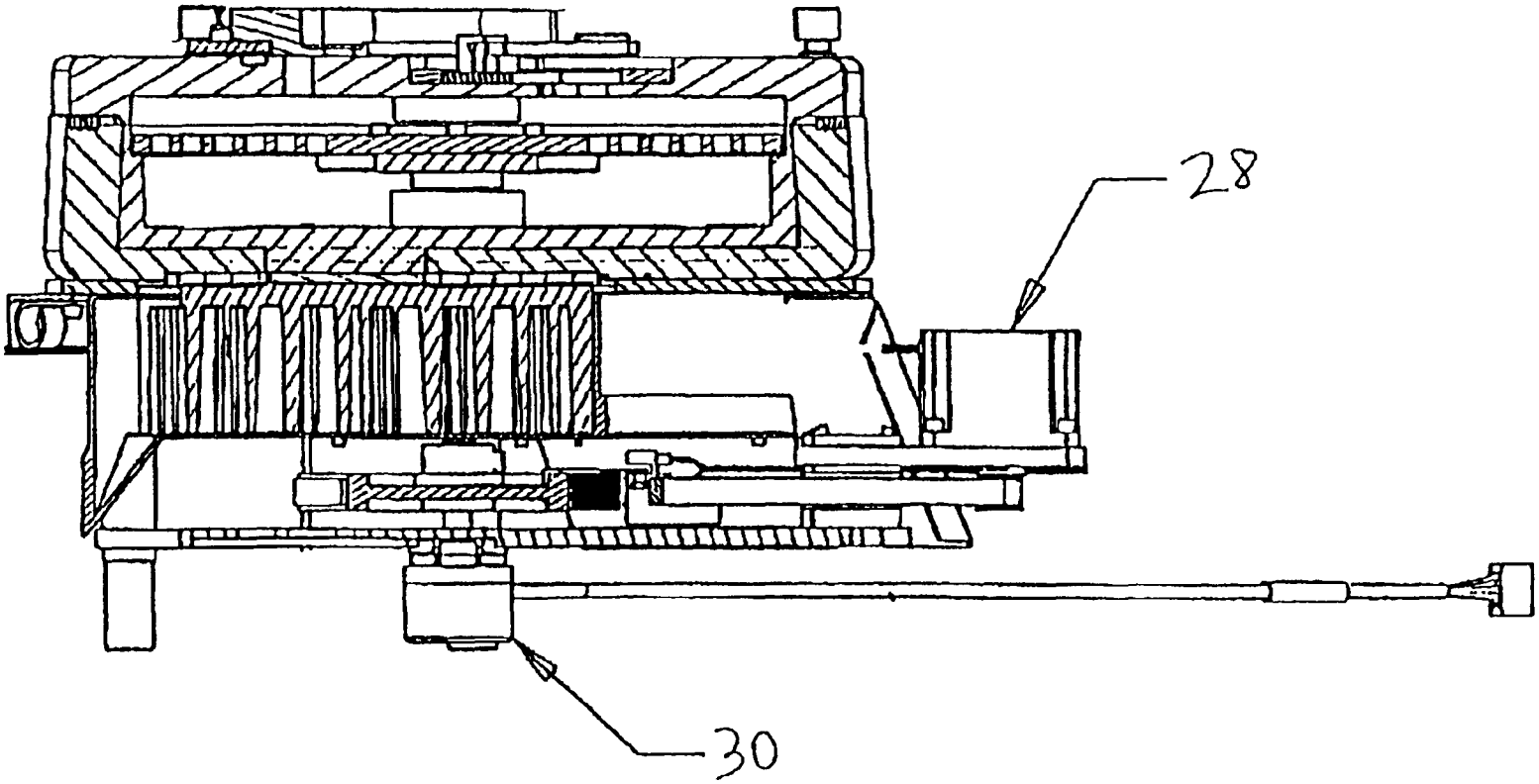
FIG. 4 is a side sectional view of one embodiment of the sample aliquot storage unit of the present invention.

Referring to FIG. 4, the sample aliquote storage unit further includes means for driving and controlling said sample storage wheel to position said sample vessels for access by the pipettor of the sample aliquoting station and the pick-and-place gripper. In accordance with one embodiment of the present invention, the driving and controlling means of said sample aliquot storage unit comprises a stepper motor 28 and an encoder 30 to accurately position the storage wheel.

The incubator/wash/read station 12 is used for the incubating, washing, and reading steps of the assays. It may include one or more incubators, washers, and readers, such as a photomultiplier tube (PMT) detector. The individual structures and functions of each of these units conform to existing arrangements of the Access Instruments (commercially available from Beckman Coulter, Inc., CA), which are known to those of ordinary skill in the art, and therefore will not be described in detail here.

The reagent storage 13 is used for storing reagents used for the assays. It serves as the means for an operator to load reagent packs into the automated immunochemistry instrument. The reagent storage 13 includes a mechanism for transporting and sorting multiple reagent packs. A detailed description of the configurations and functions of one embodiment of such a mechanism for transporting and sorting multiple reagent packs is provided in the Assignee's co-pending patent application for "Method and System for Transporting and Storing Multiple Reagent Packs and Reagent Packs Used Therein," Ser. No. 09/594,331, and is incorporated herein by reference. Other structures and functions of the reagent storage 13 conform to existing arrangements known to those of ordinary skill in the art, and therefore will not be described in detail here.

The basic operating procedures of the sample aliquot storage unit 11 of the present invention incorporated in the automated immunochemistry instrument for sample aliquot storage and reflex testing include the following steps:

1. Loading a sample tube containing a sample to be assayed to the sample presentation unit or a sample tube presented by a lab automation conveyance system;
2. Aspirating an aliquot of the sample from the sample tube by a pipettor of the sample pipetting station;
3. Placing an empty sample vessel on the sample storage wheel of the sample aliquot storage unit;
4. Positioning the empty sample vessel under the sample pipettor to receive the sample aliquot;
5. Storing the sample vessel containing sample aliquot in a chilled environment on the sample storage wheel;
6. Moving the sample vessel containing sample aliquot to one of the reagent pipetting stations by a pick-and-place gripper;
7. Aspirating an adequate amount of sample aliquot from the sample vessel for performing an assay;
8. Moving the sample vessel containing remaining sample aliquot back to the chilled sample storage wheel by the pick-and-place gripper;
9. Storing the sample vessel containing remaining sample aliquot in the chilled environment on the sample storage wheel for reflex testing;
10. When reflex testing is required, moving the sample vessel containing remaining sample aliquot to one of the reagent pipetting stations by the pick-and-place gripper;
11. Aspirating an adequate amount of sample aliquot from the sample vessel for performing the reflex testing; and
12. If there is still sample aliquot remaining and further reflex testing may be required, then moving the sample vessel containing remaining sample aliquot back to the chilled sample storage wheel for storage in the chilled environment.
13. Once it is determined that there is no further testing required on the sample aliquot, the sample vessel and any unused sample is moved to a waste container by the pick-and-place gripper.

The method and system of sample aliquot storage of the present invention for automated immunochemistry instrument has many novel and unique features and advantages. It provides the capability of performing reflex testing with a large capacity chilled sample storage area. It also supports a high throughput of the automated immunochemistry instrument. It further enables the automated immunochemistry instrument with multiple independent reagent pipetting stations to run different samples simultaneously.

A very important novel feature of the method and system of sample aliquot storage of the present invention is that, unlike in certain prior art systems where the sample vessels are always kept in the storage wheel and are pipetted in the storage wheel, in the present invention method and system, the sample vessels containing sample aliquots are transported to one of the multiplicity of reagent pipetting stations for pipetting. This transfer significantly increases the throughput of the instrument. For example, if the pipetting process takes 36 seconds, the prior art method and system will take 36 seconds to perform pipetting of each sample vessel. If there are 4 different samples to be assayed, then the total time needed to complete the pipetting process of all 4 sample vessels would be 144 seconds.

In the present invention method and system, the same task can be finished in 63 seconds. This is because in the present invention method and system, the sample vessels are transported to one of the 4 reagent pipetting stations for pipetting. These reagent pipetting stations are staggered, for example, 9 seconds apart (which is the time needed for the pick-and-place gripper to transport one sample vessel to a reagent pipetting station). As the first sample vessel is pipetted at the first reagent pipetting station, the second sample vessel is transported to the second reagent pipetting station after 9 seconds. After another 9 seconds, the third sample vessel is transported to the third reagent pipetting station. Finally, after the third 9 seconds, the fourth sample vessel is transported to the fourth reagent pipetting station. Since it takes 36 seconds to finish the pipetting process of the fourth sample vessel, the total time used for pipetting all 4 sample vessels in this example is only 63 seconds, which reduces more than half of the 144 seconds needed for the prior art method and system.

The foregoing is meant to illustrate, but not to limit, the scope of the invention. Indeed, those of ordinary skill in the art can readily envision and produce further embodiments, based on the teachings herein, without undue experimentation.

It is to be understood that the form of the system depicted in FIGS. 1 through 3 has been chosen only for the purpose of describing a particular embodiment and function of the invention, and that the arrangement of the invention can be addressed in various ways and incorporated in other types of devices, all of which will be evident to those working in the art.

It is to be understood that the particular arrangement of the present invention may vary, depending on the chemical analyzer instrument it is incorporated or working together with, but that the determination of necessary variation is well within the skill in the art in view of the instant disclosure.

Suitable components that are commercially available would be known to those of ordinary skill in the art in view of this disclosure.

It is further understood that any comparable means of accomplishing this goal is within the scope of this invention.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for automated immunochemistry or chemistry analysis, comprising:

a. a sample aliquot storage unit having a sample storage wheel;

b. a pick-and-place mechanism for transporting empty sample vessels from a bulk vessel feeder to said sample storage wheel;

c. a sample aliquoting station having a sample pipettor for aspirating samples from sample tubes loaded, and aliquoting samples to said empty sample vessels on said sample storage wheel;

d. said sample aliquot storage unit further having a chiller assembly for keeping said sample vessels containing sample aliquots in a chilled environment on said sample storage wheel;

e. said sample aliquot storage unit further having means for driving and controlling said sample storage wheel to position said sample vessels for access by said pipettor of said sample aliquoting station and said pick-and-place mechanism;

f. said pick-and-place mechanism transporting said sample vessels containing said sample aliquots to a multiplicity of independent reagent pipetting stations respectively for sample aspiration of subsequent assay; and g. said pick-and-place mechanism also transporting said sample vessels containing remaining sample aliquots back to said sample storage wheel to be stored in said chilled environment for reflex testing.

2. The apparatus as defined in claim 1, wherein said chiller assembly of said sample aliquot storage unit comprises a top cover with openings for access of said sample vessels by both said pipettor of said sample aliquoting station and said pick-and-place mechanism.

3. The apparatus as defined in claim 1, wherein said chiller assembly of said sample aliquot storage unit comprises a cold plate for establishing and maintaining said chilled environment.

4. The apparatus as defined in claim 1, wherein said chiller assembly of said sample aliquot storage unit comprises insulation means for establishing and maintaining said chilled environment.

5. The apparatus as defined in claim 1, wherein said chiller assembly of said sample aliquot storage unit comprises cooler members for establishing and maintaining said chilled environment.

6. The apparatus as defined in claim 1, wherein said chiller assembly of said sample aliquot storage unit comprises a heatsink for establishing and maintaining said chilled environment.

7. The apparatus as defined in claim 1, wherein said driving and controlling means of said sample aliquot storage unit comprises a stepper motor and an encoder to accurately position the storage wheel.

8. The apparatus as defined in claim 1, wherein said sample aliquot storage unit further comprises a base.

9. The apparatus as defined in claim 1, further comprising an incubate and wash and read unit for performing said assay.

10. The apparatus as defined in claim 9, further comprising another pick-and-place gripper for transporting vessels between said multiplicity of reagent pipetting stations and said incubate and wash and read unit.

11. The apparatus as defined in claim 1, wherein said sample pipettor of said sample aliquoting station aspirates samples from sample tubes loaded by a sample presentation unit.

12. The apparatus as defined in claim 1, wherein said sample pipettor of said sample aliquoting station aspirates samples from sample tubes presented by a lab automation system or an automated track conveyance system.

13. An apparatus for automated immunochemistry or chemistry analysis, comprising:

a. a sample aliquot storage unit having a sample storage wheel for storing sample vessels;

b. a sample aliquoting station having a sample pipettor for aliquoting samples to said sample vessels on said sample storage wheel;

c. said sample aliquot storage unit, further having a chiller assembly for keeping said sample vessels containing sample aliquots in a chilled environment on said sample storage wheel;

d. said sample aliquot storage unit, further having means for driving and controlling said sample storage wheel to position said sample vessels for access by said pipettor of said sample aliquoting station;

e. a pick-and-place mechanism for transporting said sample vessels containing said sample aliquots to a multiplicity of independent reagent pipetting stations respectively for sample aspiration of subsequent assay; and f. said pick-and-place mechanism also transporting said sample vessels containing remaining sample aliquots back to said sample storage wheel to be stored in said chilled environment for reflex testing.

14. The apparatus as defined in claim 13, wherein said sample pipettor of said sample aliquoting station aspirates samples from sample tubes loaded by a sample presentation unit.

15. The apparatus as defined in claim 13, wherein said sample pipettor of said sample aliquoting station aspirates samples directly from sample tubes presented by lab automation systems or automated track conveyance systems.

16. The apparatus as defined in claim 13, wherein said pick-and-place mechanism also transports empty sample vessels from a bulk vessel feeder to said sample storage wheel.

17. The apparatus as defined in claim 13, wherein said chiller assembly of said sample aliquot storage unit comprises a top cover with openings for access of said sample vessels by both said pipettor of said sample aliquoting station and said pick-and-place gripper.

18. The apparatus as defined in claim 13, wherein said chiller assembly of said sample aliquot storage unit comprises a cold plate for establishing and maintaining said chilled environment.

19. The apparatus as defined in claim 13, wherein said chiller assembly of said sample aliquot storage unit comprises insulation means for establishing and maintaining said chilled environment.

20. The apparatus as defined in claim 13, wherein said chiller assembly of said sample aliquot storage unit comprises cooler members for establishing and maintaining said chilled environment.

21. The apparatus as defined in claim 13, wherein said chiller assembly of said sample aliquot storage unit comprises a heatsink for establishing and maintaining said chilled environment.

22. The apparatus as defined in claim 13, wherein said driving and controlling means of said sample aliquot storage unit comprises a motor.

23. The apparatus as defined in claim 13, wherein said sample aliquot storage unit further comprises a base.

*24. An apparatus for automated immunochemistry or chemistry analysis, the apparatus comprising:*

*a sample aliquot station having a sample aliquot station pipettor configured to aspirate a sample aliquot from a sample tube and dispense the sample aliquot into a sample aliquot vessel;*

*a sample aliquot storage unit configured to store the sample aliquot vessel and comprising a controlled environment enclosure, the sample aliquot storage unit having a driver configured to position the sample aliquot vessel for access to a transport system;*

*the transport system, the transport system configured to move the sample aliquot vessel from the sample aliquot storage unit to a pipetting location, the pipetting location is separate from the sample aliquot storage unit; and*

*a pipetting station having a pipetting station pipettor configured to aspirate, at the pipetting location, an amount of the sample aliquot from the sample aliquot vessel and to dispense the amount of the sample aliquot into a reaction vessel,*

*wherein the apparatus is an automated immunoassay instrument, and*

*wherein the controlled environment enclosure refrigerates the sample aliquot vessel.*

*25. The apparatus of claim 24, wherein the transport system is capable of moving the sample aliquot vessel from the pipetting location back to the sample aliquot storage unit.*

*26. The apparatus of claim 25, wherein the reaction vessel is a first reaction vessel, wherein the transport system is further configured to aspirate a second amount of the sample aliquot from the sample aliquot vessel to a second reaction vessel.*

*27. The apparatus of claim 24, wherein the transport system is further configured to move the sample aliquot vessel from the sample aliquot storage unit to one of a plurality of pipetting locations, the pipetting locations are separate from the sample aliquot storage unit.*

*28. The apparatus of claim 24, wherein the amount is a first amount, the pipetting station is a first pipetting station, the pipetting station pipettor is a first pipetting station pipettor, and the apparatus further comprises a second pipetting station having a second pipetting station pipettor.*

*29. The apparatus of claim 28, wherein the first and second pipetting stations are configured to operate independently of each other.*

*30. The apparatus of claim 24, the apparatus further comprising a sample presentation unit configured to support the sample tube.*

*31. The apparatus of claim 24, wherein the sample aliquot storage unit includes a plurality of storage locations, the driver configured to position the sample aliquot vessel in one of the plurality of storage locations.*

*32. The apparatus of claim 24, wherein the driver is a motor.*

*33. The apparatus of claim 24, wherein the transport system is a pick-and-place mechanism.*

*34. The apparatus of claim 24, wherein the apparatus further comprises a reagent pipetting station having a reagent station pipettor configured to aspirate a reagent and dispense the reagent.*

*35. The apparatus of claim 24 wherein the sample tube is a first sample tube and the reaction vessel is a first reaction vessel, and the pipetting station is a first pipetting station and the pipetting station pipettor is a first pipetting station pipettor, and wherein the apparatus further comprises:*

*a sample presentation unit configured to support the first sample tube and a second sample tube; and*

*a second pipetting station comprising a second pipetting station pipettor configured to retrieve a reagent from a reagent pack and dispense the reagent into a second reaction vessel.*

*36. The apparatus of claim 35 wherein*

*the sample presentation unit, the sample aliquot station, the first pipetting station, and the second pipetting station are coupled together, and*

*wherein the first and second pipetting stations are configured to operate independently of each other.*

*37. The apparatus of claim 24 wherein the sample aliquot is a first sample aliquot, the sample aliquot vessel is a first sample aliquot vessel, the reaction vessel is a first reaction vessel, the pipetting station is a first pipetting station, and the pipetting station pipettor is a first pipetting station pipettor, and wherein the apparatus further comprises:*

*the first sample tube;*

*a second sample tube;*

*a sample presentation unit configured to support the first sample tube and the second sample tube;*

*wherein the sample aliquot station is further configured to aspirate a second sample aliquot from the second sample tube, and to dispense the second sample aliquot into a second reaction vessel;*

*the second reaction vessel containing the second sample aliquot; and*

*a second pipetting station configured to hold the second reaction vessel and comprising a second pipetting station pipettor,*

*wherein the first and second pipetting stations are coupled to the sample aliquot station.*

* * * * *